(12) United States Patent
Winter (10) Patent No.: US 8,069,865 B1
(45) Date of Patent: Dec. 6, 2011

(54) DISPOSABLE DENTAL FLOSSER

(76) Inventor: Lynn A. Winter, Bloomington, MN (US)

( * ) Notice: Subject to any disclaimer, the term of this patent is extended or adjusted under 35 U.S.C. 154(b) by 312 days.

(21) Appl. No.: 12/386,021

(22) Filed: Apr. 13, 2009

(51) Int. Cl.
*A61C 15/00* (2006.01)
*A61C 15/04* (2006.01)

(52) U.S. Cl. ........................................ 132/323; 132/329

(58) Field of Classification Search ................. 132/323, 132/309, 321, 324–329; 15/110, 111
See application file for complete search history.

(56) References Cited

U.S. PATENT DOCUMENTS

| | | | |
|---|---|---|---|
| 1,485,519 A * | 3/1924 | Nelson | 132/309 |
| 3,376,876 A | 4/1968 | Wicklund | |
| 4,008,727 A | 2/1977 | Thornton | |
| 4,016,891 A | 4/1977 | Kupperman et al. | |
| 4,041,962 A | 8/1977 | Johansson et al. | |
| 4,265,258 A | 5/1981 | Eaton, II | |
| 4,280,518 A | 7/1981 | Gambaro | |
| 4,332,559 A | 6/1982 | Dolinsky | |
| 4,404,978 A | 9/1983 | Withers | |
| 4,522,216 A | 6/1985 | Bunker | |
| 4,531,530 A | 7/1985 | Aiken | |
| 4,736,757 A | 4/1988 | Badoux | |
| 4,776,357 A | 10/1988 | McCullough et al. | |
| 4,807,651 A * | 2/1989 | Naydich | 132/323 |
| 4,817,642 A | 4/1989 | Lipp | |
| 4,832,062 A | 5/1989 | Grollimund et al. | |
| 4,920,992 A | 5/1990 | Preciutti | |
| 5,063,948 A | 11/1991 | Lloyd | |
| 5,113,880 A | 5/1992 | Honda et al. | |
| 5,246,021 A | 9/1993 | Katz | |
| 5,280,797 A | 1/1994 | Fry | |
| 5,388,600 A | 2/1995 | Hart | |
| 5,433,226 A | 7/1995 | Burch | |
| 5,483,982 A | 1/1996 | Bennett et al. | |
| 5,545,480 A | 8/1996 | Lalani | |
| 5,692,530 A * | 12/1997 | Bible et al. | 132/321 |
| 5,692,531 A * | 12/1997 | Chodorow | 132/323 |
| 5,738,125 A | 4/1998 | Lin | |
| 5,829,458 A | 11/1998 | Chodoro | |
| 5,970,992 A | 10/1999 | Anderson | |
| 5,975,296 A | 11/1999 | Dolan et al. | |
| 7,059,334 B2 | 6/2006 | Dougan et al. | |
| 7,171,971 B2 | 2/2007 | Ochs et al. | |
| 7,174,904 B2 * | 2/2007 | Ochs et al. | 132/323 |
| 7,204,257 B2 | 4/2007 | Crossman | |
| 7,370,658 B2 | 5/2008 | Chodoro et al. | |
| 7,487,785 B2 | 2/2009 | Dougan et al. | |
| 7,540,054 B2 * | 6/2009 | Goldstein | 15/111 |
| 2001/0054211 A1 * | 12/2001 | Cabedo-Deslierres et al. | 15/106 |
| 2004/0035440 A1 * | 2/2004 | Cheng | 132/323 |
| 2004/0040572 A1 * | 3/2004 | Chodorow | 132/323 |
| 2005/0016561 A1 * | 1/2005 | Sexson | 132/309 |

(Continued)

*Primary Examiner* — Todd Manahan
*Assistant Examiner* — Vanitha Elgart (57) ABSTRACT

A multi-strand disposable dental flosser with an improved floss strand pair arrangement. The dental flosser is an integral unit having an elongate gripping handle with a toothpick at one end, and a flosser head with two spaced apart arms at the opposite end. The floss strand pair is tautly stretched across the span between the arms and anchored securely near the tips thereof. The floss strand arrangement includes an X-configured floss strand pair, and can have at least one additional X-configured floss strand pair or at least one added single floss strand disposed slightly above the lower floss strand pair. The X-configured floss strand pair has two individual strands that are spaced apart at the ends thereof and cross together at the mid-lengths thereof. The flosser can have a tongue-cleaning edge and a tongue-cleaning surface area to enhance overall oral hygiene.

20 Claims, 4 Drawing Sheets

U.S. PATENT DOCUMENTS

| | | | |
|---|---|---|---|
| 2008/0163888 A1* | 7/2008 | Chen | 132/323 |
| 2009/0090380 A1* | 4/2009 | Culver | 132/309 |
| 2009/0188522 A1* | 7/2009 | Rau | 132/323 |
| 2010/0147326 A1* | 6/2010 | Kang | 132/323 |
| 2010/0200015 A1* | 8/2010 | Sharoff | 132/323 |

* cited by examiner

DISPOSABLE DENTAL FLOSSER

CROSS-REFERENCE TO RELATED APPLICATION

Not Applicable

FEDERALLY SPONSORED RESEARCH

Not Applicable

SEQUENCE LISTING OR PROGRAM

Not Applicable

BACKGROUND OF THE INVENTION

1. Field of the Invention

The present invention relates generally to the field of dental hygiene, and more particularly relates to dental flossing devices.

2. Description of the Prior Art

Dental hygiene is an important part of a person's overall health and cleanliness, and helps combat tooth decay, peritonitis, and halitosis. It generally includes the removal of food particles or other foreign substances and the prevention of plaque buildup on the teeth. Dental flossing has long been recognized as an effective aid for cleaning the interproximal spaces between the teeth and along the sides of the teeth where many food particles and plaque become lodged. An effective dental or oral health regimen often includes frequent brushing, flossing, and tongue scraping in order to achieve the best results.

There is a wide variety of cleaning devices and combination cleaning devices designed for oral hygiene. For example, there are a number of combination toothbrush-flosser products. Theses implements may be handy at first use, but the flosser thread usually breaks long before the toothbrush wears out, so it quickly becomes a much less useful tool. Dental flossers usually include a gripping handle and a pair of approximately parallel spaced prongs or arm-like members extending from one end of the handle. One or more strands of floss or a floss tape is stretched across the span between the two arms. The user inserts the floss strand or tape between two adjacent teeth and cleans the edges of the teeth and a portion of the sides of the teeth by rubbing the floss against the engaged areas of the teeth. The user rubs the floss up and down while exerting lateral pressure on the floss against the edges and sides of the tooth. Then the user duplicates the procedure on the adjacent tooth before proceeding to floss the next pair of adjacent teeth.

There are many flosser devices with mechanisms for self-storing, advancing, and tensioning the floss, but they are often rather complex and difficult to prepare for use. They require additional preparation and periodic cleaning, and when the floss strand breaks, it can become a time consuming process to re-thread and tension the floss. There are also some power-driven flossers and vibrating flossing devices, but their complexity and cost limits their practical appeal.

Textured dental flosses have been designed, and for some applications can have enhanced cleaning ability. There are a number of different floss configurations and textures that have been developed to provide increased friction and pressure against the edges of the teeth. Potential problems with textured floss include the difficulty of manufacturing it, and if there is an abrupt change in cross-sectional dimensions of the floss, it can be prone to breaking due to an abrupt increase in tension during use. In addition, floss segments of increased cross-section may not fit in some of the especially narrow interproximal spaces.

Examples of some representative dental flossers and dental flosses include those disclosed in the following patents:

| U.S. Pat. No. | Inventor | Issue Date |
| --- | --- | --- |
| 4,265,258 | Eaton, II | May 5, 1981 |
| 4,404,978 | Withers | Sep. 20, 1983 |
| 4,522,216 | Bunker | Jun. 11, 1985 |
| 4,832,062 | Grollimund, et al. | May 23, 1989 |
| 5,433,226 | Burch | Jul. 18, 1995 |
| 5,545,480 | Lalani | Aug. 13, 1996 |
| 5,829,458 | Chodorow | Nov. 03, 1998 |

The Eaton, II patent is for floss consisting of one or more strands having a variable thickness. This product would be relatively expensive to manufacture. With its variable thickness, one or more strands may tend to snag or catch on rough edges or especially narrow gaps between teeth. This would often result in breakage of some or all of the strands. The Withers patent is for a four-prong, two-strand flosser. It is somewhat complex and would require a certain amount of dexterity and strength by the user to manipulate it. The Bunker patent is for a flosser with and X-shaped floss arrangement, but it requires the user to replace a worn floss strand and reattach a new length of floss when a floss strand wears out. The Grollimund patent is another 4-prong, two-strand (side-by-side strands) flosser. It, like the Withers unit, is rather complex and requires special user manipulation to operate. The Burch patent is for floss with alternating hard and soft segments that may not fit very well in many interproximal spaces. The Lalani patent is for floss with varying size beads. These beads may be too large to pass through some of the gaps between the teeth, so they would provide very little, if any, advantage over uniform-diameter floss. The Chodorow patent is for a flosser with two parallel strands, one above the other. It would provide some additional flossing surface, but the additional floss surface would be higher up on the tooth (lower tooth) where it would be less effective than the bottom strand.

Although there are many different types of dental flossers and floss currently available, significant efforts continue to develop more effective, practical, and user-friendly designs to accommodate the desires of consumers.

BRIEF SUMMARY OF THE INVENTION

The present invention has been developed in view of the above-described state of the art. The primary object of the present invention is to provide a multi-strand dental flosser that cleans a larger surface of the interproximal space with each rubbing motion of the flosser. It is another object of the invention to provide a flosser that allows the user to simultaneously exert adjustable lateral pressure against both of the two adjacent tooth edges of the interproximal space. It is another object of the invention to provide a flosser that is simple, extremely easy to manufacture, and inexpensive enough to appeal to the consumer market as a disposable flosser. It is yet another object of the invention to provide a highly versatile dental flosser with a toothpick and a tongue-cleaning component for additional oral health applications.

In a preferred embodiment of the present invention, the multi-strand dental flosser includes an elongate handle with an integrally formed toothpick extending from one end, and an integrally formed flosser head extending from the opposite end. The flosser head has two approximately parallel arms with at least two strands of dental floss tautly stretched across the gap therebetween, with the ends of the floss strands securely anchored to the arms. At least one pair of floss strands is disposed in an X-configuration, with the two individual strands of the pair being spaced apart slightly at their ends, and crossing together at their mid-lengths. In the preferred embodiment, the flosser also includes a roughened tongue-cleaning surface on part of the flosser surface area. It also provides a tongue-cleaning edge to further facilitate cleaning the tongue. The dental flosser is preferably manufactured as a one-piece article by an injection molding process using thermoplastic material.

The most significant advantage of the present invention over the prior art is the result of the unique multi-strand floss arrangement with at least one pair of floss strands disposed in a criss-crossed or X-configured arrangement for the purpose of providing more effective and efficient flossing, thus requiring less time and effort by the user. Adjustable lateral pressure can be applied to the edges of the teeth by the longitudinal positioning of the flosser relative to the teeth. Using tactile feedback, the user can adjust the pressure applied to the edges and sides of the teeth. By positioning one of the flosser arms closer to the teeth, the space between the individual strands of the floss strand pair increases to exert added lateral pressure on the two adjacent teeth, and enables the user to floss both teeth simultaneously. Also, with at least two floss strands working simultaneously, a greater flosser surface area is in contact with the teeth during the flossing process. The variable spacing of the floss strands along their length can also accommodate the variation in the size of the spaces between pairs of adjacent teeth. The present invention is an extremely simple unitary design, attractive, and more efficient to use than currently available dental flossers. It can be easily and economically manufactured, and is comfortable and convenient to use. It is also quite versatile, having a toothpick, a tongue-cleaning surface area, and a tongue-cleaning edge to enhance overall oral hygiene.

The foregoing summary is a brief introduction to the present invention. Other features, objects, and advantages will become apparent from the detailed description of the invention read together with the accompanying drawings which are a material part of this invention disclosure.

BRIEF DESCRIPTION OF THE DRAWINGS

Present preferred embodiments of the invention are shown on the accompanying drawings which show, for illustration purposes only, the following figures wherein.

DETAILED DESCRIPTION OF THE INVENTION

Figure 1:
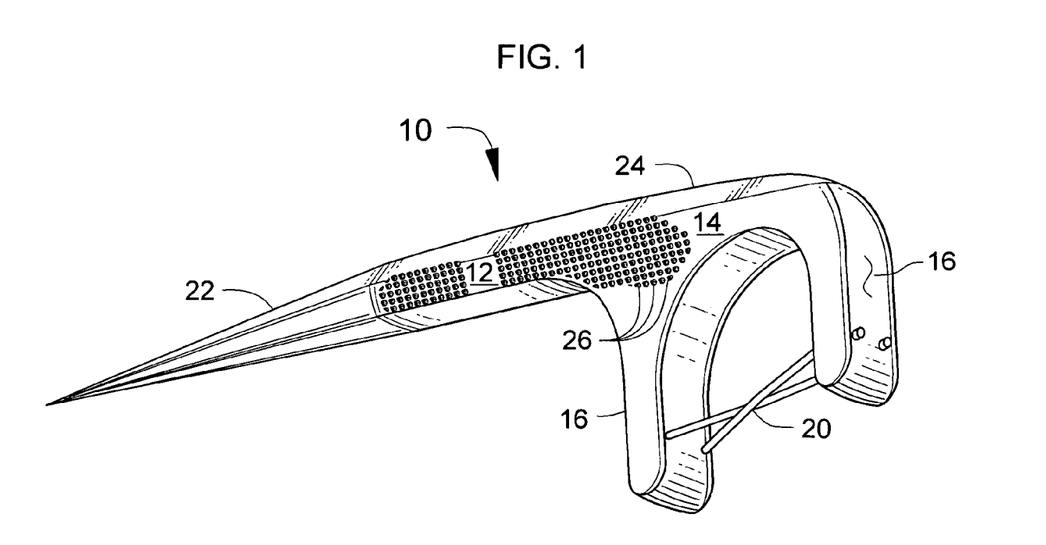
FIG. 1 is a perspective view of an integrated dental flosser, according to a preferred embodiment of the present invention, having one pair of floss strands that are criss-crossed or X-configured in a horizontal plane.
Figure 2:
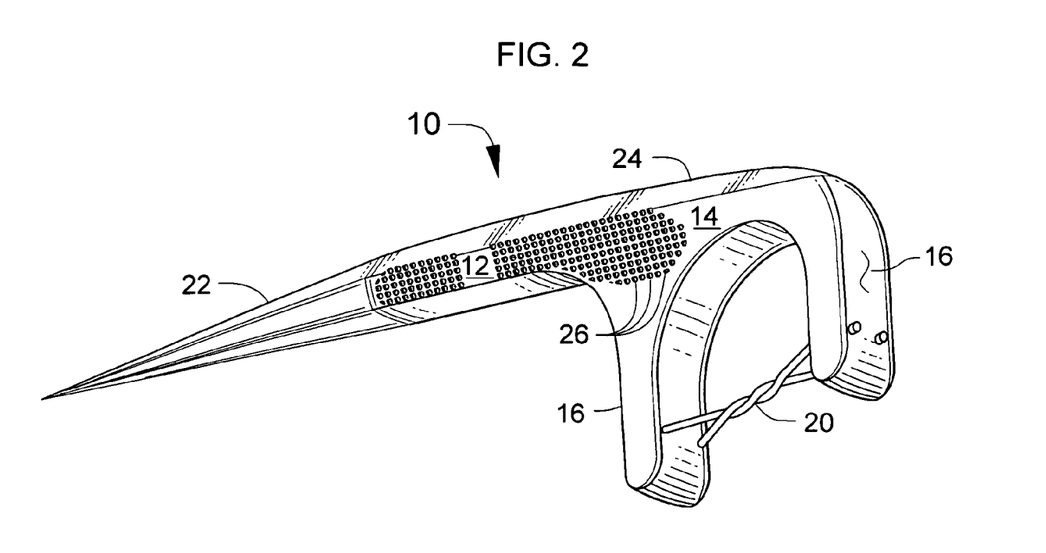
FIG. 2 is a perspective view of the dental flosser having one pair of floss strands X-configured and twisted together in a horizontal plane.
Figure 3:
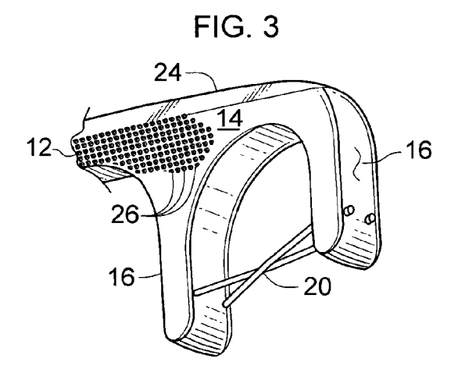
FIG. 3 is a partial perspective view of the dental flosser as illustrated in FIG. 1 having one pair of X-configured floss strands crossing together in a horizontal plane.
Figure 4:
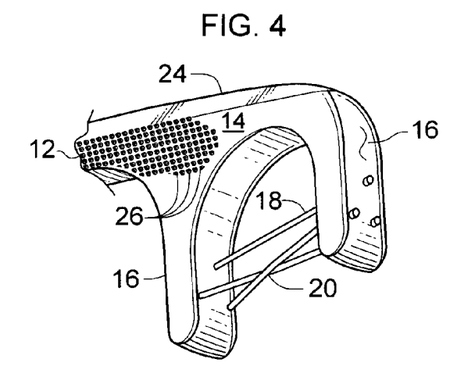
FIG. 4 is a partial perspective view of the dental flosser as illustrated in FIGS. 1 and 3, but having an addition single floss strand disposed slightly above the X-configured pair.
Figure 5:
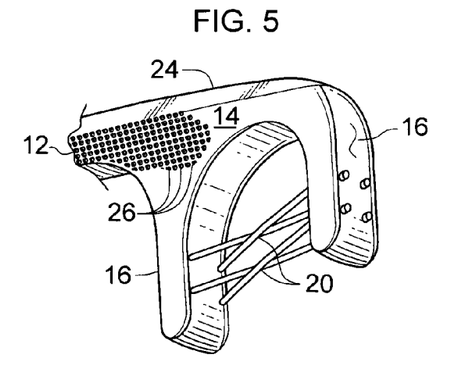
FIG. 5 is a partial perspective view of the dental flosser as illustrated in FIGS. 1 and 3, but having an additional X-configured floss strand pair disposed slightly above the first floss strand pair.
Figure 6:
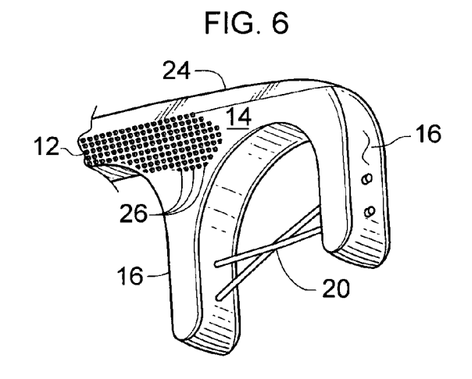
FIG. 6 is a partial perspective view of the dental flosser having one pair of floss strands X-configured in a vertical plane.
Figure 7:
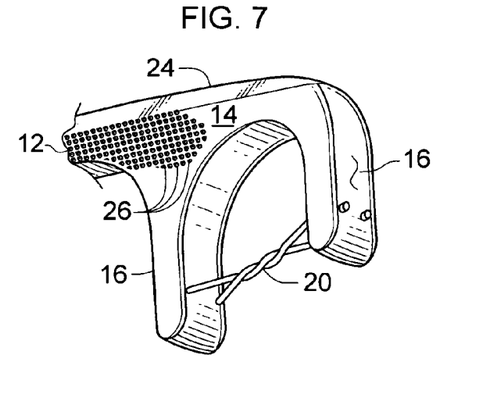
FIG. 7 is a partial perspective view of the dental flosser as illustrated in FIG. 2 having one pair of X-configured floss strands twisted together in a horizontal plane.
Figure 8:
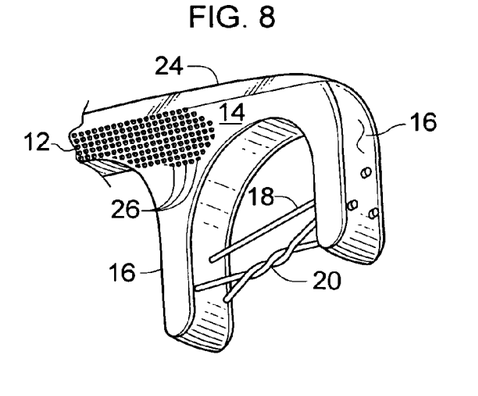
FIG. 8 is a partial perspective view of the dental flosser as illustrated in FIG. 7, but having an additional single floss strand disposed slightly above the X-configured, twisted pair.
Figure 9:
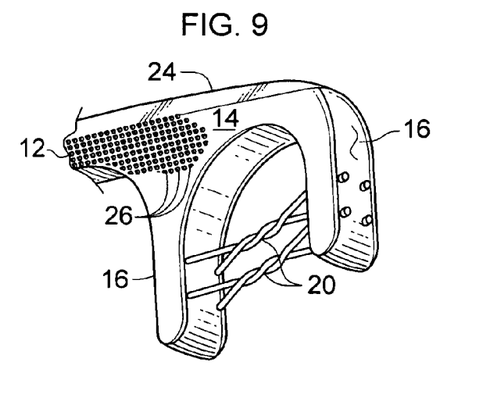
FIG. 9 is a partial perspective view of the dental flosser as illustrated in FIG. 7, but having an additional X-configured, twisted pair disposed slightly above the first floss strand pair.
Figure 10:
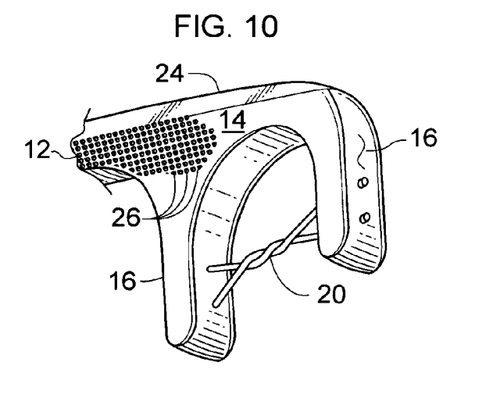
FIG. 10 is a partial perspective view of the dental flosser having one pair of X-configured floss strands twisted together in a vertical plane.
Figure 11:
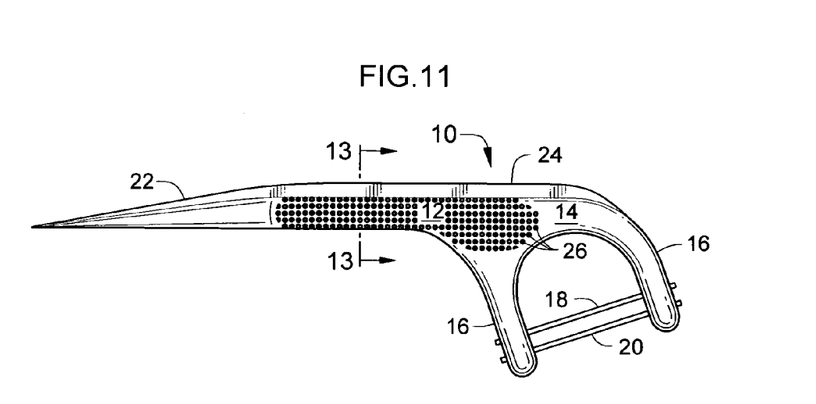
FIG. 11 is a side elevation view of the dental flosser having a tongue-cleaning edge along the top and a tongue-cleaning surface area on both sides.

With reference to the drawings, and wherein like numerals designate like parts throughout the several figures of the drawings, and with particular reference to FIG. 1, a multi-strand, integrated dental flosser 10 of the present invention is disclosed. Dental flosser 10 includes an elongate manual gripping member or handle 12. Extending longitudinally from one end of handle 12 is an integrally formed toothpick 22. At the opposite end of handle 12 is a flosser head 14. Flosser head 14 has two approximately parallel, integrally formed, spaced apart prongs or arms 16 extending obliquely or arched downwardly from flosser head 14. The arms 16 are shown in the figures as being approximately parallel to one another, but it should be noted that they can be oriented to diverge in a V-shaped or C-shaped configuration with spaced apart ends to secure the dental floss strand 18 and floss strand pair 20 stretched therebetween. At least one floss strand pair 20 is tautly stretched across the span between the two arms 16, and the ends of floss strand pair 20 are securely anchored to the arms 16 near the tips thereof Flosser 10 is a unitary structure composed of molded plastic or nylon material and is of a somewhat flattened configuration for ease in molding and convenience in handling. The flosser 10 structure is manufactured by injection molding with the floss strand 18 and floss strand pair 20 positioned in place across the span between the two arms 16. Dental flosser 10 is sized and configured to provide sufficient strength and resistance to breakage during normal use. Dental flosser 10 is of sufficient length to allow the user to comfortably clean the molars at the back of the mouth.

Figures 12, 13:
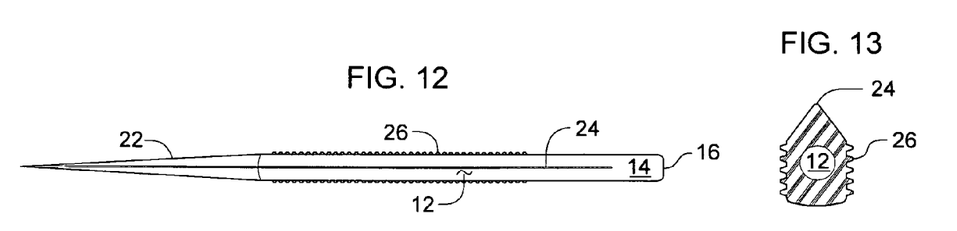
FIG. 12 is a top plan view of the dental flosser illustrated in FIG. 11.
FIG. 13 is a cross-sectional view through the handle of the dental flosser taken along Line 13-13 of FIG. 11.
Figure 14:
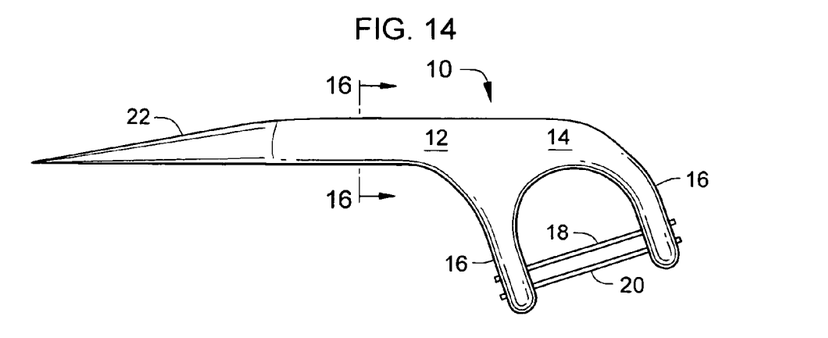
FIG. 14 is a side elevation view of the dental flosser without a tongue-cleaning edge and without a tongue-cleaning surface area.
Figure 15:
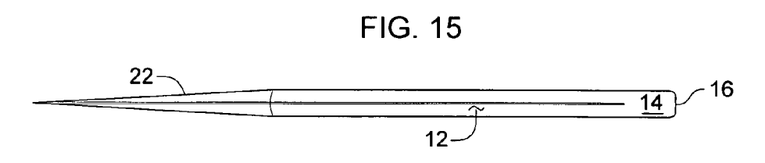
FIG. 15 is a top plan view of the dental flosser illustrated in FIG. 14.
Figure 16:
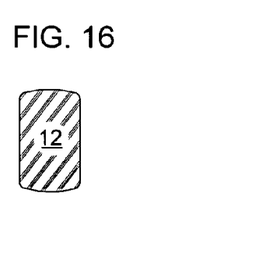
FIG. 16 is a cross-sectional view through the handle of the dental flosser taken along Line 16-16 of FIG. 14.

Handle 12 is an elongate member that serves as the handgrip portion of dental flosser 10, and is integrally formed with toothpick 22 at one end and flosser head 14 at the other end. Handle 12 is typically somewhat oval-shaped in cross-section, but can have various other cross-sectional shapes, while being of sufficient size and strength to prevent breakage during use. FIGS. 13 and 16 show typical cross-sections of handle 12.

Toothpick 22 is an elongate member tapered from one end of handle 12 to become a point at its distal end. Toothpick 22 typically transitions to a generally rounded or oval cross-section and has sufficient size and strength to preclude breakage during normal use in dislodging food particles from the interproximal spaces defined by two adjacent teeth.

The arms 16 of flosser head 14 are shaped and adapted to provide strength, rigidity, and resiliency to maintain the floss strand 18 and floss strand pair 20 in a taut condition during use. Moreover, arms 16 are of sufficient length to allow the lowest floss strand pair 20 to comfortably reach the user's gum-line without the main portion of the flosser head 14 rubbing against the top of the teeth during use.

Dental flosser 10 can also include a narrowed or relatively dull edge or tongue-cleaning edge 24 for scraping the tongue. In the preferred embodiment, this tongue-cleaning edge 24 is positioned lengthwise along the top of handle 12, but can alternatively be positioned along the outer edge of flosser head 14. Tongue-cleaning edge 24 is an integral part of dental flosser 10, and is sufficiently sharp to scrape foreign mater from the tongue without causing harm to the tongue.

Dental flosser 10 can also include a roughened surface area to function as a tongue-cleaning surface area 26. Tongue-cleaning surface area 26 may be comprised of recesses, sockets, or cavities and complimentary bumps, ribs, protrusions, or combinations thereof positioned on part of the dental flosser 10 surface. Typically, tongue-cleaning surface area 26 will be comprised of a pattern of frustoconical protrusions with rounded cross-sections with tips that are rounded sufficiently to effectively remove foreign matter from the tongue without causing damage thereto. This tongue-cleaning surface area 26 may be disposed on one or both sides of the front portion of handle 12 or on one or more sides of flosser head 14 or both. To use tongue-cleaning edge 24 or tongue-cleaning surface 26, the user applies pressure and scrapes tongue-cleaning edge 24 or tongue-cleaning surface 26 over the surface of the tongue. The user can employ tongue-cleaning edge 24 and tongue-cleaning surface area 26 in combination to effectively scrape and clean the papillae of the tongue to enhance oral cleanliness and combat halitosis.

The thread-shaped floss strand 18 and floss strand pair 20 can be made from a variety of materials having sufficient tensile strength, nick resistance, and abrasion resistance. Floss strand 18 and floss strand pair 20 may be composed of nylon, polypropylene, polyester, polyethylene, PFA, PTFE, styrene, carbon fiber or mixtures thereof. Another material with highly desirable properties is made from fiber such as that manufactured and sold under the trademark "Kevlar" by the Dupont Company of Wilmington, Del. The multi-strand combination of floss strand 18 and floss strand pair 20 may be comprised of different cross-sectional shapes, sizes and textures of floss, in combination, to provide different rubbing actions against the teeth. For example, floss strand pair 20 may be of a different size and type from a single floss strand 18 disposed slightly above floss strand pair 20. The individual floss strand 18 and floss strand pair 20 can be monofilament, multifilament or consist of interconnected fibers. Floss strand 18 and floss strand pair 20 have sufficient compressibility and a cross-section size and shape to allow insertion and longitudinal (parallel to the floss strands) movement thereof between the usually narrow interproximal spaces.

It can be seen from the drawing figures that, in each example, there is an X-configured floss strand pair 20 stretched across the lower portion of the span between arms 16. Of this floss strand pair 20, the ends of the individual strands are spaced slightly apart, but they come together to cross at the mid-lengths thereof FIG. 1 and FIGS. 3-6 show the individual strands of floss strand pairs 20 coming in contact or near contact at their mid-lengths. Alternatively, FIG. 2 and FIGS. 7-10 show these individual strands of floss strand pairs 20 twisted together at the mid-lengths thereof In addition, FIGS. 4, 5, 8, and 9 show alternate floss arrangements having either an added floss strand pair 20 (FIGS. 5 and 9) or an added single floss strand 18 (FIGS. 4 and 8) positioned above the lower floss strand pair 20. The advantage derived from having the X-configured floss strand pair 20 is to provide increased flossing surface or contact points to speed the flossing process, but more importantly, to allow the user to adjust the amount of pressure simultaneously exerted against the edges of the two adjacent teeth by moving one of the flosser arms 16 closer or farther from the teeth, thus effectively taking advantage of the changing floss strand separation or spacing between the two individual strands of the floss strand pair 20 along the length thereof. This smooth transition along the length of floss strand pair 20 minimizes the likelihood of breakage, which might result from a more abrupt change in the effective size or texture of the floss arrangement. The addition of a second X-configured floss strand pair 20 (FIGS. 5 and 9) or additional single floss strand 18 (FIGS. 4 and 8) disposed slightly above the lower floss strand pair 20 provides even more flossing surface and pressure points on the edges of the teeth. In addition, it should be noted that the tips of arms 16 must be of sufficient thickness of approximately 0.3 cm or ⅛ inch or more at the floss attachment points in order to provide sufficient separation between the individual strands of the X-configured floss strand pair 20.

Dental flosser 10 can be manufactured economically in large quantities by the injection molding process using thermoplastic materials. The floss strands 18 and floss strand pairs 20 are positioned and stretched through the mold cavities of a large array of individual molds, and the thermoplastic material is then injected into the molds filling the mold cavities and embedding the ends of the floss strands 18 and floss strand pairs 20 within the tips of the arms 16. The entire array of dental flossers 10 is molded in one operation, thus producing the unitary dental flossers 10. After removing the dental flossers 10 from the molds, the excess lengths of the floss strands 18 and floss strand pairs 20 are trimmed to the outer edges of the arms 16.

To use the dental flosser 10, the user inserts the floss between two adjacent teeth in the customary manner. With the usual downward pressure of the floss at the top of the gap between the teeth (lower teeth), the two individual strands of floss strand pair 20 will align themselves vertically, one above the other, at the mid-lengths thereof, thus enabling the user to insert floss strand pair 20 between the teeth in the same manner, and with no more difficulty, as using two identical-sized, vertically, parallel-aligned single floss strands 18. After floss strand pair 20 enters the interproximal space, the user can position dental flosser 10 to take advantage of the variable separation or spacing between the individual strands of floss strand pair 20 to simultaneously exert pressure on the contact points of the two adjacent teeth for faster and more effective flossing. By placing dental flosser 10 with the mid-lengths of the X-configured floss strand pair 20 between the two adjacent teeth, the user can effectively clean the edges of the teeth. By using tactile feedback and moving dental flosser 10 longitudinally so that one of the arms 16 is closer to the teeth, the individual strands of floss strand pair 20 will be spaced farther apart, forcing them laterally against both of the adjacent teeth while bending partially around the sides of the teeth, for effective, simultaneous cleaning of a greater area of the respective teeth. This positioning of the flosser arms 16 can also be employed to accommodate slight variations in the spacing between adjacent teeth.

In those alternate configurations wherein the floss strand pairs 20 are twisted together at the mid-lengths thereof, additional textural effect results from the twists, and can be implemented by moving dental flosser 10 longitudinally as well as up and down during use.

It is therefore relatively simple and easy for the user to apply lateral pressure (pressure transverse to the length of the floss) to the floss, and, by using tactile feedback, to adjust the amount of lateral pressure on a plurality of contact points and surface areas simultaneously to more thoroughly and efficiently perform the flossing process. The dental flosser 10, according to the above-described invention, with its unique X-configured floss arrangement, therefore, provides enhanced functionality for improved flossing speed and effectiveness for the user.

The foregoing description of the preferred embodiments has been chosen to provide illustrations of the principles of the invention. It contains many specifications that are of exemplary embodiments only. They should not be construed to limit or restrict the scope, applicability, or configuration of the invention in any way. Rather, the foregoing description provides a convenient illustration of the novel features and inventive concepts for implementing exemplary embodiments of the invention. It should be understood that various changes to the described embodiments may be made in the function and arrangement of the elements described. For example, the multi-strand dental flosser may comprise a plurality of different types, sizes, compositions, and textures of floss in combination. In addition, the tongue-cleaning surface area may comprise a combination of sockets, cavities, or recesses and complimentary bumps, ribs, or protrusions of varied shapes and positions on the flosser surface. Workers skilled in the art will recognize additions, deletions, and other modifications that can be made in form and detail without departing from the spirit and scope of the invention. Thus, the scope of the invention should be determined as set forth in the appended claims, and not by the specific examples given.

I claim:

1. A one-piece, multi-strand disposable dental flosser comprising a handle and a flosser head integrally connected to one end of said handle in a vertical plane, said flosser head further comprising an integrally connected pair of spaced apart arms, said arms being approximately parallel to each other and Protruding outwardly from said flosser head forming a gap therebetween, said flosser head further comprising at least one dental floss strand pair stretched across said gap between said arms, the ends of said at least one floss strand pair being integrally formed with and permanently anchored at the ends thereof to said arms near the tips thereof, further wherein the two individual strands of said at least one floss strand pair are laterally spaced apart at their anchoring points near said arm tips, and wherein said two individual strands of said at least one floss strand pair cross together near the mid-lengths of said two individual floss strands to form said at least one floss strand pair into an X-configuration, whereby said X-configuration being in a horizontal plane, enables the user to selectively adjust the lateral pressure exerted by said two individual floss strands against two adjacent teeth, and provides additional floss contact points on the edges of surfaces of said two adjacent teeth for more efficient, simultaneous flossing of both said two adjacent teeth, said lateral pressure being adjustable by longitudinal positioning of said floss strand pair relative to the interproximal space between said two adjacent teeth, and whereby said disposable dental flosser can be used and then disposed of without the user having to attach new floss before using or having to remove used floss after use.

2. The disposable dental flosser of claim 1 wherein said flosser head further comprises at least one additional individual floss strand, said individual floss strand being aligned vertically, slightly above said at least one X-configured floss strand pair, said at least one individual floss strand being integrally formed with and permanently anchored at the ends thereof to said arms near said tips thereof, whereby said disposable dental flosser provides at least two different types of flossing action by having at least two different vertical flossing positions.

3. The disposable dental flosser of claim 1 further wherein said two individual strands of said at least one floss strand pair are twisted together near said mid-lengths thereof, whereby said at least one floss strand pair provides a gradual transition in the amount of flossing action friction near said mid-lengths thereof.

4. The disposable dental flosser of claim 2 further wherein said two individual strands of said at least one floss strand pair are twisted together near said mid-lengths thereof, whereby said at least one floss strand pair provides a gradual transition in the amount of flossing action friction near said mid-lengths thereof.

5. The disposable dental flosser of claim 1 further comprising an elongate tongue-cleaning edge integrally formed with said handle of said disposable dental flosser.

6. The disposable dental flosser of claim 1 further comprising at least one roughened tongue-cleaning surface area integrally formed with said handle of said disposable dental flosser.

7. The disposable dental flosser of claim 1 further comprising a toothpick integrally formed with said handle of said disposable dental flosser.

8. The disposable dental flosser of claim 1 further comprising an elongate tongue-cleaning edge and at least one roughened tongue-cleaning surface area integrally formed with said handle of said disposable dental flosser.

9. The disposable dental flosser of claim 1 further comprising an elongate tongue-cleaning edge and a toothpick integrally formed with said handle of said disposable dental flosser.

10. The disposable dental flosser of claim 1 further comprising at least one roughened tongue-cleaning surface area and a toothpick integrally formed with said handle of said disposable dental flosser.

11. The disposable dental flosser of claim 1 further comprising an elongate tongue-cleaning edge, at least one roughened tongue-cleaning surface area, and a toothpick integrally formed with said handle of said disposable dental flosser.

12. The disposable dental flosser of claim 2 further comprising an elongate tongue-cleaning edge integrally formed with said handle of said disposable dental flosser.

13. The disposable dental flosser of claim 2 further comprising at least one roughened tongue-cleaning surface area integrally formed with said handle of said disposable dental flosser.

14. The disposable dental flosser of claim 2 further comprising an elongate tongue-cleaning edge and at least one roughened tongue-cleaning surface area integrally formed with said handle of said disposable dental flosser.

15. The disposable dental flosser of claim 3 further comprising an elongate tongue-cleaning edge integrally formed with said handle of said disposable dental flosser.

16. The disposable dental flosser of claim 3 further comprising at least one roughened tongue-cleaning surface area integrally formed with said handle of said disposable dental flosser.

17. The disposable dental flosser of claim 3 further comprising an elongate tongue-cleaning edge and at least one roughened tongue-cleaning surface area integrally formed with said handle of said disposable dental flosser.

18. The disposable dental flosser of claim 4 further comprising an elongate tongue-cleaning edge integrally formed with said handle of said disposable dental flosser.

19. The disposable dental flosser of claim 4 further comprising at least one roughened tongue-cleaning surface area integrally formed with said handle of said disposable dental flosser.

20. The disposable dental flosser of claim 4 further comprising an elongate tongue-cleaning edge and at least one roughened tongue-cleaning surface area integrally formed with said handle of said disposable dental flosser.

* * * * *